United States Patent
Nielsen

(10) Patent No.: US 6,939,136 B2
(45) Date of Patent: Sep. 6, 2005

(54) DENTAL BRIDGE ASSEMBLY AND BINDING AGENTS THEREFOR

(75) Inventor: Lise-Lotte Kjaerulff Nielsen, Brabrand (DK)

(73) Assignee: K L ApS, Århus (DK)

( * ) Notice: Subject to any disclaimer, the term of this patent is extended or adjusted under 35 U.S.C. 154(b) by 284 days.

(21) Appl. No.: 10/239,153

(22) PCT Filed: Mar. 22, 2001

(86) PCT No.: PCT/DK01/00197

§ 371 (c)(1), (2), (4) Date: Oct. 25, 2002

(87) PCT Pub. No.: WO01/70128

PCT Pub. Date: Sep. 27, 2001

(65) Prior Publication Data

US 2003/0124490 A1 Jul. 3, 2003

(30) Foreign Application Priority Data

Mar. 22, 2000 (DK) ........................ 2000 00486
Apr. 5, 2000 (DK) ........................ 2000 00571
May 9, 2000 (DK) ........................ 2000 00769

(51) Int. Cl.$^7$ .............................................. A61C 5/10
(52) U.S. Cl. ........................ 433/223; 264/19; 433/214
(58) Field of Search .......................... 433/213, 201.1, 433/199.1, 223, 214

(56) References Cited

U.S. PATENT DOCUMENTS 4,772,436 A    9/1988   Tyszblat

FOREIGN PATENT DOCUMENTS

WO    WO99/13795    3/1999

OTHER PUBLICATIONS

Anon.; *VITA In–Ceram Directions for use*, Presentation materials (16 pages); VITA Zahnfabrik, Postfach 13 38, D–7880 Bad Säckingen, GERMANY (undated).

Anon.; *Procera AllCeram Bridge User's Manual*; Publication (10 pages); Nobel Biocare AB, PO Box 5190, SE–402 26 Goteborg, SWEDEN (undated).

Anon.; *DC–ZIRKON: The pure ceramic*; Publication (2 pages); DCS Dental AG, Gewerbstrasse 15, Postfach 104, CH–4123 Allschwill, SWITZERLAND (undated).

Anon.; *Cercon smart ceramics*; Publication (12 pages in German); Deguusa Dental GmbH, Post fach 1364, D–63403 Hanau, GERMANY (undated).

Anon.; *VITA In–ceram Spinell*; Misc. advertising materials (16 pages in German); VITA Zahnfabrik H. Rauter GmbH, Postfach 1338, D–79704 Bad Säckingen, GERMANY (undated).

Anon.; *CEREC inLab*; Advertising material (12 pages in German); Sirona dental Systems GmbH, Fabrikstrasse 31, D–64625 Bensheim, GERMANY (undated).

*Primary Examiner*—Cary E. O'Connor
*Assistant Examiner*—Candice C. Stokes
(74) *Attorney, Agent, or Firm*—James Creighton Wray; Meera P. Narasimhan

(57) ABSTRACT

In the formation of dental bridges, the preferred material is a tightly-sintered aluminium oxide, and it is normal practice that the necessary bridge parts, namely two bridge anchors and a connecting intermediate link (pontic), are formed by a specialist and thereafter joined together in a dental laboratory where use is made of a melted glass as binding agent, after which the assembled bridge item is fired with porcelain. With the invention it has been found that considerable advantages can be achieved when a dispersion of said aluminium oxide or a material related herewith is used as binding agent, which after application between the assembly surfaces is heated until loose sintering is achieved, after which an infiltration of the sintered material by the glass is brought about by renewed or additional heating. There is hereby achieved a more simple working process as well as a stronger binding both between the assembly surfaces as well as between the bridge item and the porcelain with which it is fired. The binding agent is preferable mixed with an adhesive material which eases the intermediate work with the bridge item, and which is completely degassed by the heating in the said sintering process.

20 Claims, No Drawings

DENTAL BRIDGE ASSEMBLY AND BINDING AGENTS THEREFOR

This application claims the benefit of Danish Application No. 2000 00486 filed Mar. 22, 2000, Danish Application No. 2000 00571 filed Apr. 5, 2000, Danish Application No. 2000 00769 filed May 9, 2000 and PCT/DK01/00197 filed Mar. 22, 2001.

BACKGROUND OF THE INVENTION

The present invention relates to the manufacture of dental bridges of aluminium oxide, which is currently one of the preferred materials for this purpose. A practice has been developed by which the dentist prepares the two supporting teeth (implants) as anchors for the intended bridge, and thereafter takes an impression of the relevant area by using a decidedly form-stable impression material, in that the impression shall subsequently be used for the manufacture of both a master model and a fireproof model.

The impression is transferred to a dental laboratory where a mould is made for the manufacture of a master model in hard plaster. A duplicate mould of the master model is made for later manufacture of an individual fireproof support model, a so-called "firing table".

Hereafter, the bridge is modelled up in a three-part formation comprising the two bridge anchors and a connecting intermediate link (pontic), of which the latter can, however, be prefabricated, with certain directions concerning dimensions for the transition areas between the three sections. Thereafter, these transition areas are cut over with a plane cut in accordance with a more detailed direction regarding the angle, and the three parts are sent to a specialist for the manufacture of the bridge parts in tightly-sintered aluminium oxide. However, in modern practice it is a preferred alternative that a three-dimensional scanning be carried out of the mould of the bridge parts, whereby one can suffice with a quick electronic transmission of the relevant scanning data to said specialist, who subsequently reproduces the parts in aluminium oxide.

The dental laboratory will then receive the three bridge parts which, after a possible grinding-off of excess material, are temporarily joined together, e.g. with cyanailite glue, after which a fireproof "pilot model" of the bridge is made. The already-mentioned individual "firing table" is also made for use as support element in the subsequent firing of porcelain on the assembled bridge. The fireproof material is allowed to set, after which both models are placed in a special kiln for degassing, which must be programmed in accordance with the directions for the selected fireproof material.

With the known technique, use is made of glass powder as a binding agent, which in aqueous suspension is formed as a ball which is placed on top of the relevant assembly areas, after which the glass is activated by suitable heating in an ordinary porcelain kiln, in that the glass is hereby sucked down between the assembly areas.

The thus assembled bridge frame is removed for final processing. During the subsequent, ordinary porcelain firing, the item must be supported on the said, pre-prepared "firing table", in that the glass binding in the assembly areas becomes unstable at the firing temperature.

It has been ascertained that although it is used to a wide extent, this method is not particularly ideal, in that it is very work-demanding and results in products which have a breaking strength which is not satisfactory. Many attempts have been made to improve it, but hitherto without significant results. Primarily, the solution will be to find an improved binding agent, but although highly-developed binding agents and great expertise already exist in the dental field, the result has always been that the "molten glass" has hitherto remained the agent which is used.

SUMMARY OF THE INVENTION

With the invention it has been found that a perfect binding agent consists of a material related to the bridge material and an already-known moulding material, namely in the form of loosely-sintered aluminium oxide or a corresponding sinterable material with glass infiltration. In its finished form, this material can bear comparison with the above-mentioned tightly-sintered aluminium oxide, but it is suitable for producing in the laboratory as the material does not need to be compressed. It can be shaped in suspended form and thereafter vitrified, after which a dispersion of glass powder is applied to the resulting sinter body, the glass powder being melted by a renewed or increased heating for infiltration of the glass in the loosely-sintered binding agent.

With the invention, no independent body is formed in the relevant second material, in that the material is formed laboratory-wise only as a binding agent between the main parts of the bridge frame and the tightly-sintered material. This gives rise to two important conditions, firstly that the product appears with a distinct and quite surprising increased breaking strength, and secondly that in the manufacturing process, such a good form stability of the assembled bridge frame is achieved that this, by the incorporating of a flammable adhesive in the binding agent, is suitably firm for handling for transfer to a sintering furnace and becomes fully heat-resistant after the said sintering, so that thereafter the item can freely be further processed and re-heated respectively for glass infiltration of the binding agent and final firing of porcelain, without the production and use of the said "firing table" being necessary.

Aluminium oxide with an adhesive for formation of an initial binding between the bridge parts can be applied with a brush to the assembly surfaces as a watery paste, respectively by modelling-in between the assembly surfaces. After a quite short drying period, there will be achieved such an initial binding that the assembled item can be transferred without any special form stabilisation to an ordinary firing kiln which does not require vacuum connection, and in which a sintering of the binding material is effected, for example for two hours at approx. 1140° with a rise of ½ an hour.

Hereafter, the assembled bridge frame is thoroughly stable for handling, and it can be removed for possible grinding as required and subsequent application of an aqueous glass-powder mass around the assembly areas.

Thereafter, the actual glass infiltration can be effected, e.g. in the already mentioned ordinary firing kiln, in that here it is sufficient to place the item on fire cotton or in another loosely supported or suspended manner. A firing at approx. 1140° for two hours with a rise of ½ an hour can be typical, but the main thing is that the firing is concluded when the loosely-sintered aluminium oxide has absorbed that amount of glass it can accommodate.

The glass infiltration can well be carried out in the utilised simple firing kiln in direct extension of the sintering, in that the glass mass can be placed on the bridge item in local accumulations at the assembly areas in such a manner that these accumulations will remain firm at the sintering temperature, and are first brought to melt at an increased temperature of around 1200° when the sintering has been completed. The glass material will hereby not have any blocking effect against emission of the gases which are released by the sintering, and the glass infiltration can be brought about solely by a further heating of the kiln in one and the same firing sequence. Thereafter, the bridge will be totally stable for handling.

It shall be noted that the expression "glass infiltration" is a trade expression which, while although referring to the material "glass", is not however limited entirely to this material (felspar), in that it can also embrace other materials with high melting point and corresponding infiltration and reinforcement characteristics.

After this processing, the bridge frame can be removed for sandblasting of a possible distinct surplus of glass, and thereafter a "glass control firing" can be effected, e.g. at 970° for 10 minutes for the release of a possible surplus of glass, which can thus also be removed. Thereafter, the bridge frame can be given a final polishing.

The bridge frame will thus be ready for a quite conventional application and firing with porcelain, and whereby it will not be necessary to make use of any individual "firing table", as the bridge frame will already be completely form-stable during exposure to the associated temperatures.

The finished bridge appears with an increased and in practice a fully acceptable breaking strength with regard to pressure and torsional influences, and it will be produced by a considerably simplified process.

The invention has certain additional advantages on more specific planes, such as with a modelling-up or out of the binding material on the assembly surfaces, in the event of an under-dimensioning of these, an extended assembly surface can be achieved which not only reinforces the assembly in itself, but also provides an improved adhesion to the outer porcelain. It applies for the binding agent or the product according to the invention that this will adhere better than pure glass both to tightly-sintered metal oxides and porcelain.

The invention will embrace both the described method, the described "two-stage binding agent" and that product which as intermediate product or finished product displays one or more assemblies effected in accordance with the invention.

With the invention it has been found that the described binding material shall not necessarily consist solely of aluminium oxide, in that it has been found that there can be other material candidates such as zirconium oxide as a full or partial replacement for aluminium oxide. For the time being, it must merely stand as a condition that use is made of a suitable "binding agent material", which in lightly sintered form can be infiltrated by glass or a corresponding ceramic material. Other candidates for the binding agent will be various commercial ceramic materials, namely metal oxides, which can well be available as mixing materials.

As mentioned, with the invention the use of the known "firing table" can be omitted, but there is naturally nothing to prevent use being made of a formed firing table anyway. The demands can hereby be reduced regarding the initial binding, which shall be exercised by the discussed paste of the binding material, in that in this paste there can be mixed an active binding agent, e.g. gelatine or water-soluble adhesive, which will provisionally ensure the necessary binding together, but which with certainty will be burned away in the subsequent sintering process. It applies in general that the demands regarding the said initial binding will be reduced by use of the "firing table".

Certain of the relevant sinterable materials will give lower breaking strengths than with the best materials, but super-high breaking strengths can well give rise to problems with regard to the removal of hitherto bridge parts, and for this reason it will often be acceptable to use weaker materials.

It will thus be understood that the method and the binding agent according to the invention will not be bound up with quite certain materials, but rather with the characteristics of these materials, and hereby that the invention will also apply with the possible appearance of new materials with relevant characteristics.

What is claimed is:

1. Method for the preparation of dental bridges of sintered material fired with porcelain, by which on the basis of an impression of a relevant implant area there is formed a physical or virtual bridge item in a three-part formation comprising two bridge anchors and a connecting intermediate link (pontic), which parts are reproduced in a tightly-sintered oxide and thereafter bound together with a binding agent for the formation of a bridge frame on which a hard ceramic coating is fired, wherein as a binding agent use is made of a suspension of basic material for formation of said tightly-sintered material, namely aluminium oxide, zirconium oxide or other metal oxides, which can be sintered and infiltrated with glass, and in that the hereby assembled bridge frame is heated for direct sintering of the applied binding agent, after which the thus stabilized self-supporting bridge item, at least in the assembly areas, is given an application of a dispersion of a powder of an infiltration material of glass which, with renewed heating in the bridge frame, is brought to melting and infiltration in the sinter-fired binding agent.

2. Method according to claim 1, wherein as binding agent use is made of a moulding mass based on one or more metal oxides such as aluminium or zirconium oxide or other metal oxides or mixtures hereof.

3. Method according to claim 1, wherein the binding agent is mixed with one or more additional binding components such as gelatin or dissolved adhesive, which are dispersed by the heating in the subsequent sintering process.

4. Method according to claim 1, wherein the bound-together bridge frame parts are transferred for heating of the binding agent in the sintering process without any additional mutual support.

5. Dental bridge frame item executed as a glued-together three-part formation of two bridge anchors and a connecting intermediate link (pontic) with respective adjoining connection surfaces, between which there is embedded a binding agent, wherein said embedded binding agent comprises glass and a metal oxide.

6. Dental bridge frame item according to claim 5, wherein said metal oxide is an aluminum oxide or zirconium oxide.

7. A method for preparing dental bridges comprising obtaining an impression of a desired implant area, forming a bridge corresponding to the impression of title implant area, the bridge including two bridge anchors and a connecting intermediate link, heating and directly sintering the binding agent material, forming the bridge with the sintered binding agent material, stabilizing the bridge, applying glass powder material, re-heating, sintering, melting, dispersing and infiltrating the glass in the sintered binding agent, and forming a self-supporting bridge.

8. The method of claim 7, wherein the forming with the material comprises forming with metal oxides.

9. The method of claim 8, wherein the forming further comprises molding a mass of one or more of the metal oxides.

10. The method of claim 8, wherein the forming further comprises selecting metal oxides suitable for sintering and infiltrating with glass.

11. The method of claim 9, wherein the forming further comprises selecting metal oxides from the group consisting of aluminum oxide, zirconium oxide, and combinations thereof.

12. The method of claim 11, wherein the forming further comprises molding a mass of one or more of the metal oxides.

13. The method of claim 7, wherein the forming further comprises mixing the binding agent with one or more additional binding components, heating the mixture and sintering, and dispersing the binding components therethrough.

14. The method of claim 13, wherein the additional binding components are selected from the group consisting of gelatin, dissolved adhesive, flammable adhesive, and combinations thereof.

15. The method of claim 7, further comprising transferring the bound-together self-supporting bridge and heating the binding agent by sintering without additional mutual support for the bridge.

16. The method of claim 15, further comprising firing the sintered self-supporting bridge with a ceramic coating.

17. A self-supporting dental bridge frame apparatus comprising a three-part frame including two bridge anchors and a connecting intermediate link, the link having respective adjoining connection surfaces, a binding agent embedded between the connection surfaces, and a self-supporting bridge frame formed by sintering the binding agent and the frame.

18. The apparatus of claim 17, wherein the embedded binding agent comprises metal oxides selected from the group consisting of aluminum oxide, zirconium oxide, and combinations thereof.

19. The apparatus of claim 17, further comprising glass material infiltration in the binding agent.

20. The apparatus of claim 18, further comprising additional binding components selected from the group consisting of gelatin, dissolved adhesive, flammable adhesive, and combinations thereof.

* * * * *